US008097583B2

(12) United States Patent
Scheibel et al.

(10) Patent No.: US 8,097,583 B2
(45) Date of Patent: Jan. 17, 2012

(54) PROTEINS OF NATURAL ORIGIN AND MATERIALS MADE THEREFROM

(75) Inventors: Thomas Scheibel, Munich (DE); Daniel Huemmerich, Mannheim (DE)

(73) Assignee: Amsilk GmbH, Munich (DE)

( * ) Notice: Subject to any disclaimer, the term of this patent is extended or adjusted under 35 U.S.C. 154(b) by 46 days.

(21) Appl. No.: 11/643,200

(22) Filed: Dec. 21, 2006

(65) Prior Publication Data

US 2007/0196429 A1  Aug. 23, 2007

Related U.S. Application Data

(63) Continuation of application No. PCT/EP2005/006799, filed on Jun. 23, 2005.

(60) Provisional application No. 60/583,227, filed on Jun. 25, 2004.

(30) Foreign Application Priority Data

Mar. 11, 2005 (EP) ..................................... 05005395

(51) Int. Cl.
  *C07K 14/00* (2006.01)
  *A61K 38/00* (2006.01)
  *A61F 13/00* (2006.01)
(52) U.S. Cl. .............................. 514/2; 530/350; 424/426
(58) Field of Classification Search ........................ None
  See application file for complete search history.

(56) References Cited

U.S. PATENT DOCUMENTS

| 5,994,099 A | 11/1999 | Lewis et al. |
| 6,280,747 B1 | 8/2001 | Philippe et al. |
| 7,157,615 B2 | 1/2007 | Karatzas et al. |
| 2007/0214520 A1* | 9/2007 | Scheibel et al. .............. 800/288 |
| 2008/0021553 A1* | 1/2008 | Scheibel et al. .............. 623/13.2 |

FOREIGN PATENT DOCUMENTS

| WO | WO 99/47661 | 9/1999 |
| WO | WO 03/020916 | 3/2003 |
| WO | WO03/057727 A1 | 7/2003 |
| WO | WO03/060099 A | 7/2003 |
| WO | WO-03057727 A1 * | 7/2003 |

OTHER PUBLICATIONS

Gatesy et al. Extreme diversity, conservation, and convergence of spider silk fibroin sequences. *Science*, vol. 291, (2001), pp. 2603-2605.
Guerette et al. Silk properties determined by gland-specific expression of a spider fibroin gene family. *Science*, vol. 272, (1996), pp. 112-115.
Hinman et al. Synthetic spider silk: a modular fiber. *Tibtech*, vol. 18, (2000), pp. 374-379.
Huemmerich et al. Novel assembly properties of recombinant spider dragline silk proteins. *Current Biology*, vol. 14, (2004), pp. 2070-2074.

International Search Report corresponding to PCT application No. PCT/EP05/06905.
Knebel et al. The promoter of the late p10 gene in the insect nuclear polyhedrosis virus *Autographa californica*: activation by viral gene products and sensitivity to DNA methylation. *The EMBO Journal*, vol. 4, No. 5, (1985), pp. 1301-1306.
Lazaris et al. Spider silk fibers spun from soluble recombinant silk produced in mammalian cells. *Science*, vol. 295, (2002), pp. 472-476.
Li et al. The natural silk spinning process A nucleation-dependent aggregation mechanism? *European Journal of Biochemistry*, vol. 268, (2001), pp. 6600-6606.
Lombardi et al. The amino acid composition of major ampullate gland silk (dragline) of *Nephila glavipes*(araneae, tetragnathidae). *Journal of Arachnology*, vol. 18, (1990), pp. 297-306.
Parkhe et al. Structural studies of spider silk proteins in the fiber. *Journal of Melecular Recognition*, vol. 10, (1997), pp. 1-6.
Scheller et al. Production of spider silk proteins in tobacco and potato. *Nature Biotechnology*, vol. 19, (2001), pp. 573-577.
Shao et al. The effect of solvents on spider silk studied by mechanical testing and single-fibre Raman spectroscopy. *International Journal of Biological Macromolecules*, vol. 24, (1999), pp. 295-300.
Simmons et al. Solid-state 13C NMR of *Nephila clavipes* dragline silk establishes structure and identity of crystalline regions. *Macromolecules*, vol. 27, (1994), pp. 5235-5237.
Van Beek et al. The molecular structure of spider dragline silk: Folding and orientation of the protein backbone. *Proceedings of the National Academy of Sciences of USA*, vol. 99, No. 16, (2002), pp. 10266-10271.
Wong Po Foo at al. Genetic engineering of fibrous proteins: spider dragline silk and collagen. *Advanced Drug Delivery Reviews*, vol. 54, (2002), 1131-1143.
Yamao et al. Gene targeting in the silkworm by use of a baculovirus. *Genes and Development*, vol. 13, (1999), pp. 511-516.
Communication Pursuant to Article 94(3) EPC corresponding to European Patent Application No. 05 753 637.7-1212 dated Sep. 1, 2008.
Fahnestock et al., "Synthetic Spider Dragline Silk Proteins and Their Production of *Escherichia coli*," Appl. Microbiol. Biotechnol., vol. 47, pp. 23-32 (1997).
Service et al., "Mammalian Cells Spin a Spidery New Yarn," Science, vol. 295, pp. 41-42 (Jan. 18, 2002).
Summons (dated Jul. 27, 2009) to Attend Oral Proceedings in European App. No. 05753637.7.
Park et al., J. Biosci Bioeng, 87 (1999) 756-761.
Ohgo et al. Polymer 44 (2003) 846-6.

(Continued)

*Primary Examiner* — Anand Desai
(74) *Attorney, Agent, or Firm* — Baker & Daniels LLP

(57) ABSTRACT

The present invention is directed to proteins of natural origin and materials made therefrom, in particular to threads, fibers, foams and gels derived therefrom. The invention further provides the use of these proteins/threads and materials in the field of technology, biotechnology and/or medicine, in particular in the manufacture of wound closure or coverage systems, suture materials and in the manufacture of replacement materials, preferably artificial cartilage or tendon materials, as well as in other commercial applications.

11 Claims, 6 Drawing Sheets

OTHER PUBLICATIONS

Lewis et al., Protein Expression and Purification 7 (1996) 400-6.
International Preliminary Report on Patentability corresponding to PCT application No. PCT/EP05/06799.
International Search Report corresponding to PCT application No. PCT/EP05/06799 dated Aug. 31, 2005.
Masafumi Yamao et al. Gene targeting in the silkworm by use of a baculovirus. *Genes and Development*, vol. 13, No. 5, (1999), pp. 511-516.
Written Opinion of the International Searching Authority corresponding to PCT application No. PCT/EP05/06799.

* cited by examiner

FIGURE 1
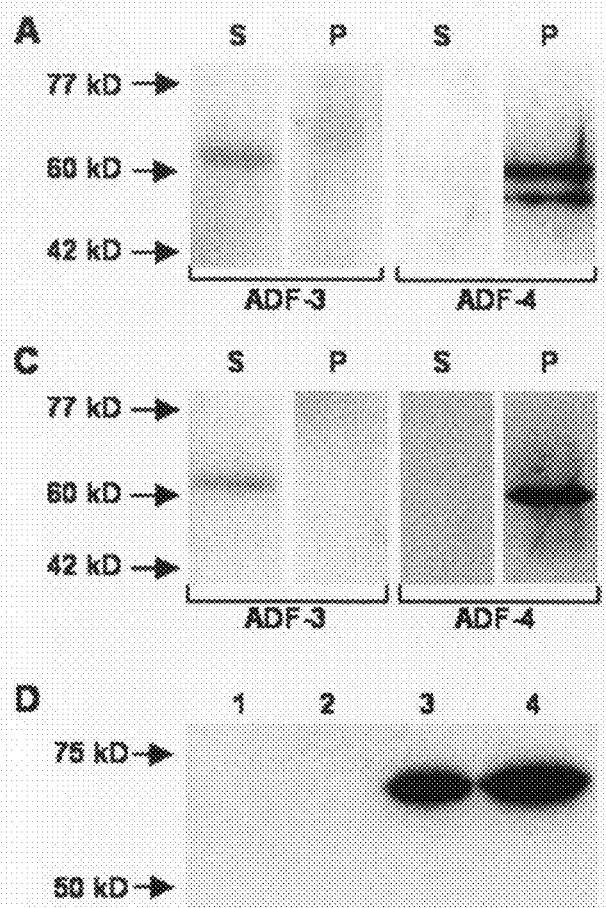
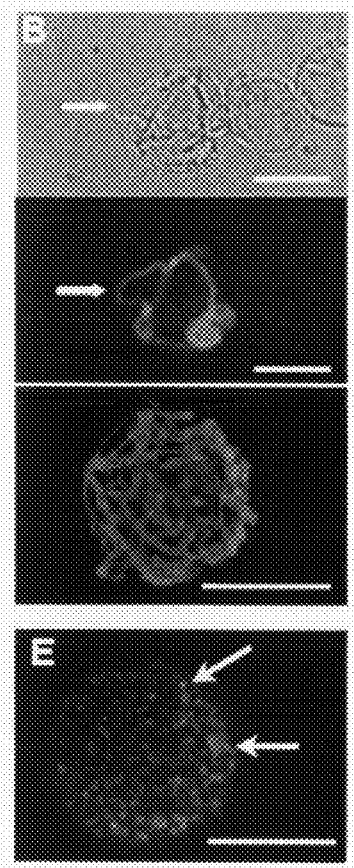

FIGURE 4
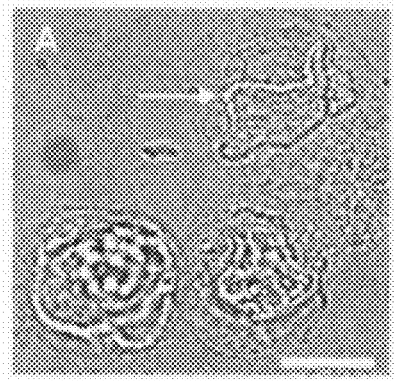 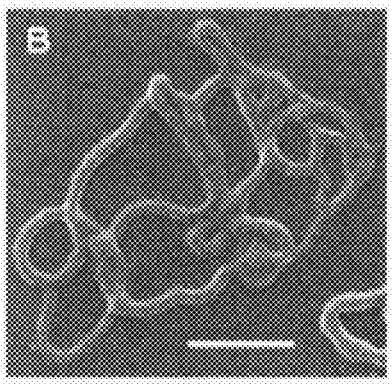
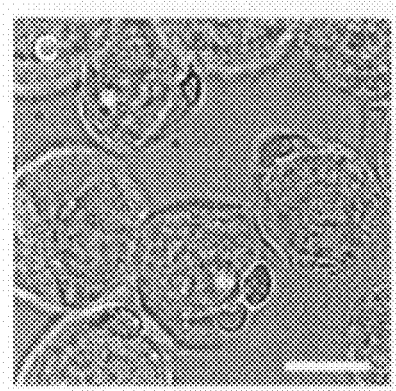 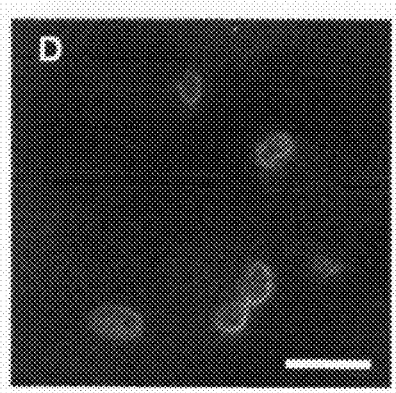
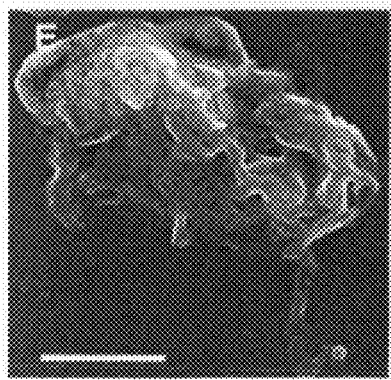

US 8,097,583 B2

PROTEINS OF NATURAL ORIGIN AND MATERIALS MADE THEREFROM

RELATED APPLICATIONS

This application is a continuation of PCT International Patent Application No. PCT/EP2005/006799, filed Jun. 23, 2005, which claims priority to U.S. Provisional Patent Application No. 60/583,227, filed Jun. 25, 2004 and European Patent Application No. 05005395.8, filed Mar. 11, 2005, the disclosures of each of which are incorporated herein by reference in their entirety.

BACKGROUND

The present invention is directed to proteins of natural origin and materials made therefrom, in particular threads, fibers, foams and gels derived therefrom. The invention further provides the use of these proteins/threads and materials in the field of biotechnology and/or medicine, in particular in the manufacture of wound closure or coverage systems, suture materials and in the manufacture of replacement materials, preferably artificial cartilage or tendon materials, as well as in other commercial applications.

Spider dragline silk has extraordinary properties (1) originating in its composition as a semi crystalline polymer (2) that contains crystalline regions embedded in an amorphous matrix. X-ray diffraction and NMR show the crystalline regions to consist of pleated beta sheets of polyalanine stretches which are giving strength to the thread (3,4), while the predominant secondary structure of the amorphous matrix is a glycine rich $3_1$ helix providing elasticity (5). Freshly secreted silk proteins are stored at high concentrations (6) as a liquid crystalline dope (7,8) that is altered by changes in ionic composition, pH (from pH 6.9 to 6.3) (9,10) and water extraction (10,11) during its passage through the spinning duct to be finally converted into a solid thread induced by extensional flow (12).

All dragline silks studied so far consist of at least two different proteins with molecular masses of up to several hundred kDa (13). The individual contribution of the two major dragline silk proteins of *Araneus diadematus*, ADF-3 and ADF-4, to dragline thread assembly and structure has not been determined so far. Analyzing the primary structures revealed that ADF-3 and ADF-4 (14,15) have similar proline contents and polyalanine motifs, but they differ in glutamine and serine content as well as in length of the glycine-rich regions. Importantly, the properties of silk threads cannot be inferred from the underlying protein sequences. Although the quality of a silk thread is based on the primary structure of the involved proteins, it further depends on the silk assembly process (8), which necessitates experimental analysis of structural and assembly properties.

Scientific and commercial interest initiated the investigation of industrial scale manufacturing of spider silk. Native spider silk production is impractical due to the cannibalism of spiders, and artificial production has encountered problems in achieving both sufficient protein yield and quality thread-assembly. Bacterial expression yielded low protein levels (16), likely caused by a different codon usage in bacteria and in spiders. Synthetic genes with a codon usage adapted to the expression host led to higher yields (13,17), but the proteins synthesized thereof showed different characteristics in comparison to native spider silks. Expression of partial dragline silk cDNAs in mammalian cell lines did yield silk proteins (e.g. ADF-3) that could be artificially spun into 'silken' threads, albeit as yet of inferior quality (18).

WO03060099 relates to methods and devices for spinning biofilament proteins into fibers. This invention is particularly useful for spinning recombinant silk proteins from aqueous solutions and enhancing the strength of the fibers and practicality of manufacture such as to render commercial production and use of such fibers practicable. Therein, it is disclosed to express spider silk proteins in mammalian cells, e.g. transgenic goat mammary gland cells.

SUMMARY

Therefore, it is an object of the present invention to provide an improved starting material, i.e. protein, for the manufacture of spider silk threads, fibers and other materials in high yield and superior quality. Additional objects are to provide new proteins/threads and further materials based on spider silk proteins and/or other naturally derived materials for use in biotechnology, medicine and for other commercial purposes.

These objects are solved by the subject-matter of the independent claims. Preferred embodiments are set forth in the dependent claims.

Regarding the drawbacks of the prior art methods, which are related to the production of spider silk proteins and threads derived therefrom, a different and more efficient route to synthesize authentic spider silk proteins may be used.

Spider dragline silk, which exhibits extraordinary strength and toughness, is primarily composed of two related proteins whose role in thread assembly and whose contribution to the mechanical properties of dragline threads is largely unknown. In order to elucidate this role, a baculovirus expression system was used by the inventors to produce recombinant ADF-3 and ADF-4, the two major dragline silk proteins of the garden spider *Araneus diadematus*, in host insect cells. It was shown that ADF-4, but not ADF-3 readily self-assembled into filaments in the cytosol of the cells. These ADF-4 filaments displayed the exceptional chemical stability typical for authentic spider dragline silk threads. As a result, the properties of ADF-4 show its role as the structural key player in dragline silk.

Thus far, little is known about the structure, function and possible interplay between the two major protein components of spider dragline silk threads. The inventors observed that, despite their similarities in primary structure, ADF-3 and ADF-4 display surprisingly different properties. Whilst, ADF-3 represents an intrinsically soluble protein, ADF-4 is virtually insoluble under the experimental conditions employed and forms filamentous aggregates in the cytoplasm of Sf9 cells with a chemical stability comparable to natural dragline threads. The similarities between ADF-4 filaments and native dragline silk threads suggest that ADF-4 is the structural 'key player' in dragline threads providing its chemical and physical strength. Since thread formation has to be fast at natural reeling speeds of 1-10 cm/s (19), an easily assembling compound, such as ADF-4, is mandatory for silk formation. However, the tendency of ADF-4 to aggregate implies that other factors within the spinning dope are likely required to keep it from premature polymerization in the gland. These factors are likely to be post-translational modifications such as phosphorylation and glycosylation. Additionally, ADF-4's solubility could be influenced by proteins that are co-secreted and also stored in the dope. Although ADF-3 did not influence solubility of ADF-4 within the cytosol of the insect cells, it may still play an important role in regulating ADF-4 solubility during or after secretion from the spider gland. The specific conditions present in the secretory pathway of the spider gland cells as well as in the glands' lumen may lead to interactions between ADF-3 and ADF-4, which regulates silk thread assembly.

Spider silks can be regarded as the benchmarks for future polymer design not only due to their superb quality but are also preferred since they could be produced economically and in an environment-friendly way from aqueous solvents under ambient temperatures and pressures. However, major barriers remain our ability to match the native silk fiber production process. The results provided herein constitute the essential basis for elucidating the function and interplay of the two major components of spider silk dragline proteins, e.g. of *Araneus* dragline silk, ADF-3 and ADF-4. Such knowledge is essential for spinning silk threads from recombinant proteins and for production of a new generation of fibrous materials.

In the context of the present invention, a method of producing spider silk dragline proteins derived from the major ampullate gland may be used, comprising the following steps:
a) providing a nucleic acid sequence coding for one or more spider dragline proteins,
b) introducing the nucleic acid sequence(s) provided in a) into an insect cell,
c) expressing the dragline proteins; and
d) recovering said dragline proteins.

Thus, as mentioned above, one of the major advantages offered by this method resides in the provision of an expression system for spider silk dragline proteins, i.e. the expression in insect cells. It surprisingly turned out that, as explained above, the expression of those proteins in insect cells is superior to the expression in other cells, as, for example, bacterial cells and mammalian cells. This improvement equally affects the quality, i.e. mechanical properties and the like, as well as the yield of spider silk dragline proteins.

As an example, according to the method of ref. 16, 4 mg/l of cells were obtained, which could not be spun into threads; in ref. 18, 25 mg/l of cells (threads were obtained, however, had poor quality). By the present method, >30 mg/l of cells could be obtained (self-assembling, stabile thread).

The dragline proteins encoded by the nucleic acid sequence provided in step a) of the above method are preferably selected from dragline proteins of orb-web spiders (Araneidae).

Such dragline proteins may be derived from one or more of the following spiders: *Arachnura higginsi, Araneus circulissparsus, Araneus diadematus, Argiope picta*, Banded Garden Spider (*Argiope trifasciata*), Batik Golden Web Spider (*Nephila antipodiana*), Beccari's Tent Spider (*Cyrtophora beccarii*), Bird-dropping Spider (*Celaenia excavata*), Black-and-White Spiny Spider (*Gasteracantha kuhlii*), Black-and-yellow Garden Spider (*Argiope aurantia*), Bolas Spider (*Ordgarius furcatus*), Bolas Spiders—Magnificent Spider (*Ordgarius magnificus*), Brown Sailor Spider (*Neoscona nautica*), Brown-Legged Spider (*Neoscona rufofemorata*), Capped Black-Headed Spider (*Zygiella calyptrata*), Common Garden Spider (*Parawixia dehaani*), Common Orb Weaver (*Neoscona oxancensis*), Crab-like Spiny Orb Weaver (*Gasteracantha cancriformis* (elipsoides)), Curved Spiny Spider (*Gasteracantha arcuata*), *Cyrtophora moluccensis, Cyrtophora parnasia, Dolophones conifera, Dolophones turrigera*, Doria's Spiny Spider (*Gasteracantha doriae*), Double-Spotted Spiny Spider (*Gasteracantha mammosa*), Double-Tailed Tent Spider (*Cyrtophora exanthematica*), *Aculeperia ceropegia, Eriophora pustulosa*, Flat Anepsion (*Anepsion depressium*), Four-spined Jewel Spider (*Gasteracantha quadrispinosa*), Garden Orb Web Spider (*Eriophora transmarina*), Giant Lichen Orbweaver (*Araneus bicentenarius*), Golden Web Spider (*Nephila maculata*), Hasselt's Spiny Spider (*Gasteracantha hasseltii*), *Tegenaria atrica, Heurodes turrita*, Island *Cyclosa* Spider (*Cyclosa insulana*), Jewel or Spiny Spider (*Astracantha minax*), Kidney Garden Spider (*Araneus mitificus*), Laglaise's Garden Spider (*Eriovixia laglaisei*), Long-Bellied *Cyclosa* Spider (*Cyclosa bifida*), Malabar Spider (*Nephilengys malabarensis*), Multi-Coloured St Andrew's Cross Spider (*Argiope versicolor*), Ornamental Tree-Trunk Spider (*Herennia ornatissima*), Oval St. Andrew's Cross Spider (*Argiope aemula*), Red Tent Spider (*Cyrtophora unicolor*), Russian Tent Spider (*Cyrtophora hirta*), Saint Andrew's Cross Spider (*Argiope keyserlingi*), Scarlet *Acusilas* (*Acusilas coccineus*), Silver *Argiope* (*Argiope argentata*), Spinybacked Orbweaver (*Gasteracantha cancriformis*), Spotted Orbweaver (*Neoscona domiciliorum*), St. Andrews Cross (*Argiope aetheria*), St. Andrew's Cross Spider (*Argiope Keyserlingi*), Tree-Stump Spider (*Poltys illepidus*), Triangular Spider (*Arkys clavatus*), Triangular Spider (*Arkys lancearius*), Two-spined Spider (*Poecilopachys australasia*), Nephila species, e.g. *Nephila clavipes, Nephila senegalensis, Nephila madagascariensis* and many more (for further spider species, see also below). *Araneus diadematus* is most preferred.

Preferably, the dragline proteins produced by this method are the dragline proteins wild type ADF-3, ADF-4, MaSp I, and/or MaSp II. The term ADF-3/-4 is used in the context of MaSp proteins produced by *Araneus diadematus* (*Araneus diadematus* fibroin-3/-4). Both proteins, ADF-3 and -4 belong to the class of MaSp II proteins (major ampullate spidroin II).

Further spider silk proteins, which can be produced by this (i.e. alone or in combination with further proteins) and their database accession numbers are:
spidroin 2 [*Araneus bicentenarius*]gi|2911272
major ampullate gland dragline silk protein-1 [*Araneus ventricosus*] gi|27228957
major ampullate gland dragline silk protein-2 [*Araneus ventricosus*]gi|27228959 ampullate spidroin 1 [*Nephila madagascariensis*]gi|13562006
major ampullate spidroin 1 [*Nephila senegalensis*] gi|13562010
major ampullate spidroin 1 [*Latrodectus geometricus*] gi|13561998
major ampullate spidroin 1 [*Argiope trifasciata*]gi|13561984
major ampullate spidroin 1 [*Argiope aurantia*]gi 13561976
dragline silk protein spidroin 2 [*Nephila clavata*] gi|16974791
major ampullate spidroin 2 [*Nephila senegalensis*] gi|13562012
major ampullate spidroin 2 [*Nephila madagascariensis*] gi|13562008
major ampullate spidroin 2 [*Latrodectus geometricus*] gi|13562002

The invention is in particular directed to the following aspects and embodiments:

According to a first aspect, the present invention is directed to a spider dragline protein, which is encoded by the nucleic acid sequence of SEQ ID NO: 1 or 2, or variants of those nucleic acid sequences, which variants are each defined as having one or more substitutions, insertions and/or deletions as compared to the sequence of SEQ ID NO: 1 or 2, provided that said variants hybridize under moderately stringent conditions to a nucleic acid which comprises the sequence of SEQ ID NO: 1 or 2, or provided that said variants comprise nucleic acid changes due to the degeneracy of the genetic code, which code for the same or a functionally equivalent amino acid as the nucleic acid sequence of SEQ ID NO: 1 or 2.

The term "nucleic acid sequence" refers to a heteropolymer of nucleotides or the sequence of these nucleotides. The terms "nucleic acid" and "polynucleotide" are used interchangeably herein to refer to a heteropolymer of nucleotides.

Stringency of hybridization, as used herein, refers to conditions under which polynucleotide duplexes are stable. As known to those of skill in the art, the stability of duplex is a function of sodium ion concentration and temperature (see, for example, Sambrook et al., Molecular Cloning: A Laboratory Manual $2^{nd}$ Ed. (Cold Spring Harbor Laboratory, (1989)). Stringency levels used to hybridize can be readily varied by those of skill in the art.

As used herein, the phrase "moderately stringent conditions" refers to conditions that permit DNA to bind a complementary nucleic acid that has about 60% identity, preferably about 75% identity, more preferably about 85% identity to the DNA; with greater than about 90% identity to said DNA being especially preferred. Preferably, moderately stringent conditions are conditions equivalent to hybridization in 50% formamide, 5×Denhart's solution, 5×SSPE, 0.2% SDS at 42° C., followed by washing in 0.2×SSPE, 0.2% SDS, at 65° C.

It is noted that two different kinds of ADF-3 and ADF-4 coding sequences are contemplated in this invention: first, the already published sequence of ADF-3 and ADF-4 (herein: "wild type" sequence) and, second, a variant thereof, encoded by SEQ ID NO: 1 (ADF-3) and 2 (ADF-4). The wild type sequences were already published and are available under the accession numbers U47855 and U47856 (SEQ ID NO: 3 and 4).

As explained above, the silk fiber has crystalline regions of β-sheets interspersed with elastic amorphous segments similar to liquid crystalline polymers. These two segments are represented by two different proteins, MaSp I (major ampullate spidroin I) and MaSp II (major ampullate spidroin.II) coded by different genes.

The nucleic acid sequence of the present invention is preferably ADF-3, ADF-4 (SEQ ID NO: 1 and 2) or a variant thereof. SEQ ID NO: 3 and 4 are showing the corresponding amino acid sequences of the wild type sequences.

According to a preferred embodiment, the method of the present invention provides spider silk proteins consisting of a polymer, the building blocks thereof being defined as one or more of the proteins as defined above or a variant of said proteins. The amino acid sequences of the proteins of the present invention also encompass all sequences differing from the herein disclosed sequences by amino acid insertions, deletions, and substitutions.

Preferably, amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

"Insertions" or "deletions" are typically in the range of about 1 to 5 amino acids, preferably about 1, 2 or 3 amino acids. Amino acid additions typically are not more than 100, preferably not more than 80, more preferably not more than 50, most preferred not more than 20 amino acids, which are added on and/or inserted into the proteins of the present invention. It is noted that only those additions are contemplated in this invention, which do not negatively affect the mechanical and further characteristics of the proteins disclosed herein.

The variation allowed may be experimentally determined by systematically making insertions, deletions, or substitutions of amino acids in a protein using recombinant DNA techniques and assaying the resulting recombinant variants for activity. This does not require more than routine experiments for the skilled artisan.

According to a preferred embodiment, one or more of the nucleic acid sequences defined above are contained in a vector. Preferably, this vector is an expression vector, which comprises the nucleic acid sequence coding for one or more dragline proteins as defined above and one or more regulatory sequences. Such regulatory sequences may preferably comprise promoters p10 and/or polyhedrin, but other late and very late baculoviral promoters can be used as well.

The vector is more preferably a viral vector, most preferably a baculovirus vector system or a vaccinia virus vector system. Further viral vector systems may also be used in this invention. From case to case, a modification of the vector may be needed. Examples for further viral vectors are adenoviruses and all negative-strand RNA-viruses, e.g. rabies, measles, RSV, etc.

As insect cells, *Lepidoptera* insect cells may preferably be used, more preferably cells from *Spodoptera frugiperda* and from *Trichoplusia ni*. Most preferably, the insect cell is a Sf9, Sf21 or high five cell.

One advantage of insect cell expression system, for example regarding bacterial systems, resides in the fact that the proteins produced are glycosylated, thereby being a target for degradation by microorganisms. This characteristic may be of importance, for example, in the field of medicine, whenever the silk proteins are intended for an in vivo use, in which biological degradation is desired. This characteristic may in particular find application in suture materials and wound closure and coverage systems.

According to a further preferred embodiment, the only dragline protein expressed is wild type ADF-4 or ADF-4 encoded by SEQ ID NO: 2.

As an alternative, the only dragline protein expressed is wild type ADF-3 or an amino acid encoded by the nucleic acid of SEQ ID NO: 1 as a dragline protein.

The inventors surprisingly found out that, in contrast to the conviction of the prior art, only one of the two known major dragline proteins (preferably ADF-4) is needed for the manufacture and assembly of a dragline silk thread. Therefore, the already known approaches for the manufacture of dragline silks can be considerably simplified by using only one component for preparing the dragline silk instead of two, as it is known in the art. Thus, a dragline silk consisting of only ADF-3 and, preferably, only ADF-4, is a preferred embodiment of the invention.

Class MaSp I can be distinguished from MaSp II by the content of amino acid proline. Within the class of MaSp II, no further official subranges are existing. However, ADF-3 and ADF-4 are differing from each other by their content of amino acid glutamine and in the spacing and length of the polyalanine regions. Therefore, one of skill in the art can easily determine those regions in MaSp II, which are corresponding to ADF-3 and ADF-4, respectively.

Preferably, the expression of said dragline proteins occurs by secretory expression. For further explanation, see chapter Examples. Alternatively, the expression occurs by cytoplasmatical production. As it is shown in the Examples, the conditions, which are present in the insect cells used for expression led to the surprising result that—as mentioned above—spider silk proteins were expressed in high yield an good quality and, moreover, a self-assembly of those proteins to threads occurred already in the cytoplasm without any further production step.

In the context of the present invention a method for producing spider dragline protein threads can be used, comprising the following steps:

a) expressing spider dragline proteins as defined above,
b) recovering said proteins, and
c) spinning said proteins into threads by a suitable method.

In step c), spinning methods may be used, which are per se known in the art. For example, a dope solution of spider silk protein is extruded through a spinneret to form a biofilament. The resulting biofilament can be drawn or stretched. Whenever both crystalline and amorphous arrangements of molecules exist in biofilaments, drawing or stretching will apply shear stress sufficient to orient the molecules to make them more parallel to the walls of the filament and increase the tensile strength and toughness of the biofilament.

The dope solution may contain a mixture of silk proteins from one or more spider species, or silk proteins from different silk-producing genera, for example, a mixture of silk proteins from spiders and *B. mori*. In the most preferred embodiments, the silk proteins are dragline silks from *N. clavipes* or *A. diadematus*, particularly the proteins MaSpI, MaSpII, ADF-3, and ADF-4. In alternate embodiments, the dope solution contains a mixture of silk proteins and one or more synthetic polymers or natural or synthetic biofilament proteins.

Preferably, the dope solution is at least 1%, 5%, 10%, 15% weight/volume (w/v) silk protein. More preferably, the dope solution is as much as 20%, 25%, 30%, 35%, 40%, 45%, or 50% w/v silk protein. In preferred embodiments, the dope solution contains substantially pure spider silk protein. In preferred embodiments, the dope has a pH of approximately 6.9.

By "dope solution" is meant any liquid mixture that contains silk protein and is amenable to extrusion for the formation of a biofilament or film casting. Dope solutions may also contain, in addition to protein monomers, higher order aggregates including, for example, dimers, trimers, and tetramers. Normally, dope solutions are aqueous solutions of pH 4.0-12.0 and having less than 40% organics or chaotropic agents (w/v). Preferably, the dope solutions do not contain any organic solvents or chaotropic agents, yet may include additives to enhance preservation, stability, or workability of the solution.

By "filament" is meant a fiber of indefinite length, ranging from microscopic length to lengths of a mile or greater. Silk is a natural filament, while nylon and polyester as an example are synthetic filaments.

By "biofilament" is meant a filament created (e.g., spun) from a protein, including recombinantly produced spider silk protein.

Further information regarding how to spin spider silk protein fibers may be found in WO03060099 (Karatzas et al.), published Jul. 24, 2003, which is incorporated herein by reference.

The invention further encompasses a spider dragline protein or thread, comprising an amino acid sequence encoded by the nucleic acid of SEQ ID NO: 1 and/or 2; or a variant thereof.

In a preferred embodiment, the spider dragline protein/thread only comprises wild type ADF-4 or an amino acid encoded by the nucleic acid of SEQ ID NO: 2 as a dragline protein.

As an alternative, the spider dragline protein/thread only comprises wild type ADF-3 or an amino acid encoded by the nucleic acid of SEQ ID NO: 1 as a dragline protein.

According to a further aspect, the invention provides a gel or a foam comprising or consisting of a protein as defined hereinabove. An example on how to produce such foams and gels may be found in the Examples, see chapter "Assembly of spider silk derived proteins" below.

Furthermore, the present invention is directed to coatings for implants and stents comprising or consisting of a protein of the invention as defined above. The coatings can be made of soluble proteins, films, gels, foams, nanofibrils, and threads, depending on the respective usage. In general, protein coatings on non-biological materials such as ceramics, metal, plastic, etc. "hide" the non-biological surface preventing inflammatory response or rejection by the body. The protein coatings will allow cell binding, which will enclose the non-biological material. Furthermore, a reduction of implantation-related inflammation can be effected by selection of those graft materials that are inherently more biocompatible than those heretofore employed in stent-graft devices. Conventional graft materials such as PET polyester and nylon have high solubility factors which indicate that the material is prone to higher rates of solubilization within native vessels and therefore more prone to inflammatory responses.

The materials of the present invention exhibit desirable characteristics which inhibit the inflammatory responses observed with other conventional polymeric materials used in stent-graft applications.

The invention further provides a thread or fiber, comprising a protein, thread or fiber as defined above and a further material or fiber, not being of spider origin and preferably being a plant derived material or fiber. For example, a mixed fiber of spider silk proteins and cotton could be advantageous.

Further fibers to be used include one or more of nylon, aramide, keviar, wool, carbon fibers, collagen fibres, cellulose, keratin fibers, elastin fibers, gum and the like.

A vector, which comprises a nucleic acid coding for wild-type ADF-4 as only dragline protein or which comprises the nucleic acid of SEQ ID NO: 1 and/or SEQ ID NO: 2 is provided in the present invention as a further aspect.

In a still further aspect, a baculovirus vector is provided, which comprises a nucleic acid coding for one or more dragline proteins, preferably for the dragline proteins ADF-3, ADF-4 (wild type), ADF-3 (SEQ ID NO:1) and/or ADF-4 (SEQ ID NO:2).

As already explained above, the proteins/threads as defined herein may be used in the field of biotechnology and/or medicine, preferably for the manufacture of wound closure or coverage systems, suture materials for use in neurosurgery or ophthalmic surgery.

Surprisingly, it turned out that the proteins of the present invention and the fibers, threads and further materials made therefrom, show anti-microbial, in particular anti-bacterial properties. Bearing in mind their inherent biodegradability, they have the optimal characteristics for in vivo applications in humans or animals. Thus, by using the present proteins and the materials derived therefrom, noxious influences on the body during surgery may be minimized, additional surgery may be avoided and reconvalescence following surgery may be accelerated.

Furthermore, the proteins/threads may preferably be used for the manufacture of replacement materials, preferably artificial cartilage or tendon materials.

A further use is for the stabilization of artificial replacements, preferably artificial replacement lungs.

Additionally, the threads/fibers of the invention can be used in the manufacture of medical devices such as medical adhesive strips, skin grafts, replacement ligaments, and surgical mesh; and in a wide range of industrial and commercial products, such as clothing fabric, bullet-proof vest lining, container fabric, bag or purse straps, cable, rope, adhesive binding material, non-adhesive binding material, strapping material, vehicle covers and parts, construction material, concrete, paint, polysiloxane, weatherproofing material, flexible partition material, sports equipment; and, in fact, in nearly any use of fiber or fabric for which high tensile strength and elasticity are desired characteristics. Adaptability and use of the stable fiber product in other forms, such as a dry spray coating, bead-like particles, or use in a mixture with other compositions is also contemplated by the present invention.

Unless otherwise defined, all technical and scientific terms used herein have the same meaning as commonly understood by one of ordinary skill in the art to which this invention pertains. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention is now further illustrated by Examples and the accompanying drawings, which are showing the following:

BRIEF DESCRIPTION OF THE DRAWINGS

FIG. 1 Expression of adf-3 (SEQ NO: 1) and adf-4 (SEQ NO: 2) in Sf9 cells. (A) Solubility of ADF-3 and ADF-4 after synthesis. Soluble (S) and insoluble components (P) of cell lysates were separated by sedimentation. Proteins were detected by immunoblotting with an anti-His$_6$ antibody. (B) Filament in adf-4 expressing cell, as seen with light microscopy (upper panel) and with fluorescence microscopy after immunocytochemistry (middle panel). An additional confocal fluorescence image after immunocytochemistry of another cell is shown in the lower panel. Scale bars: 10 µm. (C) Solubility of co-synthesized ADF-3 and ADF-4. Soluble (S) were separated from insoluble (P) cell components by sedimentation. ADF-3 was detected with S-protein-peroxidase conjugates after western blotting and ADF-4 with anti-T7-tag antibodies. (D) Sf9 cells in suspension were infected with the mel-His$_6$-adf-4 virus. At the indicated times (in days post infection) aliquots equivalent to 6×10$^4$ cells were taken from the culture media, centrifuged to remove cells and subjected to SDS-PAGE followed by immunoblotting. (E) Cells infected for 3 days with the mel-his$_6$-adf-4 virus were subjected to immunofluorescence. Secretion vesicles on the cell surface could be clearly detected. Scale bar 10 µm.

FIG. 4 (A) Filaments of ADF-4 without His$_6$-tag formed within Sf9 cells were visualized by light microscopy. (B) The morphology of filaments obtained after dual expression of adf-3 (SEQ NO: 1) and adf-4 (SEQ NO: 2) was investigated by scanning electron microscopy. (C) adf-3 (SEQ NO: 1) expressing Sf9 cell were imaged by light microscopy. (D) Cellular localization of ADF-3. Cells infected for 3 days with adf-3 (SEQ NO: 1) viruses were subjected to immunofluorescence analysis. (E) ADF-4 aggregates formed after renaturation in vitro visualized by scanning electron microscopy. (F) Chemical stability of ADF-4 aggregates formed in vitro. After treatment with denaturants, as indicated, solubilized ADF-3 was detected by immunoblotting. Scale bars 5 µm (B,E) and 10 µm (A,C,D).

DETAILED DESCRIPTION

Examples

Figure 2:
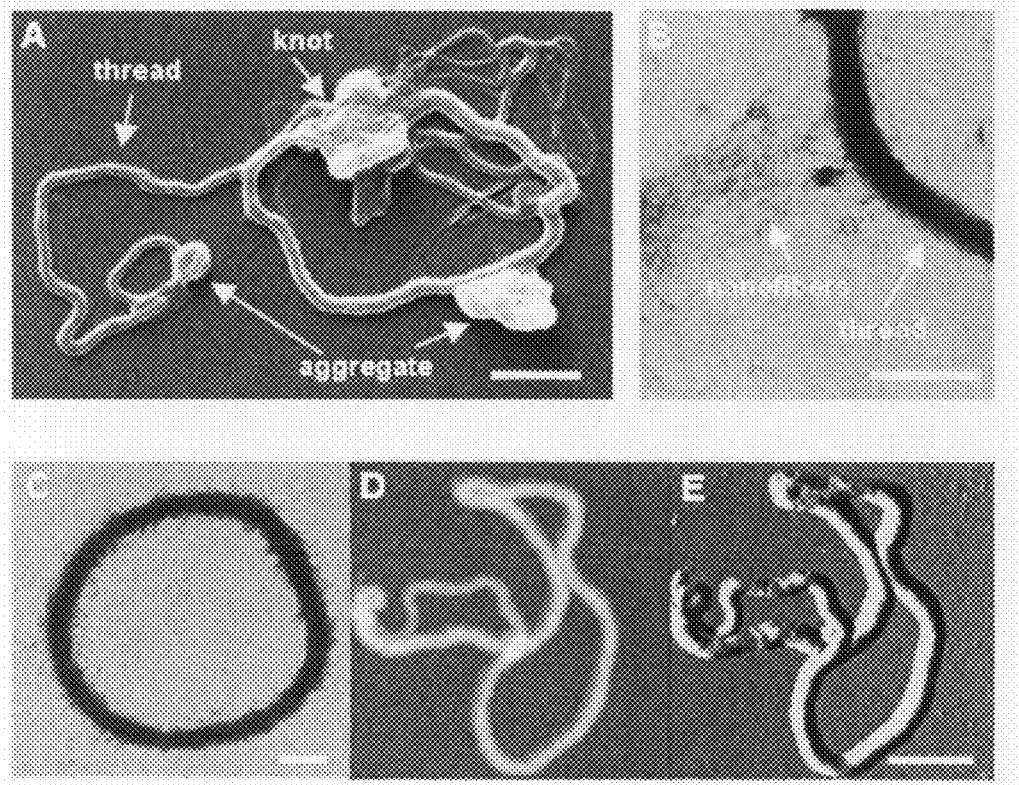
FIG. 2 Morphology of ADF-4 filaments and aggregates. (A) Scanning electron microscopy on purified filaments. Scale bar: 5 µm (B) Transmission electron microscopy on purified filaments. Scale bar: 500 nm (C) Immunoelectron microscopy on purified filaments using mouse anti-His$_6$ antibodies followed by gold-conjugated anti-mouse antibodies. Scale bar: 500 nm (D, E) Atomic force microscopy (AFM): (D) height image (E) deflection image. The height of the filament is 0.7 µm. Scale bar 5 µm.

The improvement provided herein was based on the idea to express and study the two major protein constituents of *Araneus diadematus* dragline silk simultaneously. Since insects belong to the same phylum as spiders, the inventors chose the insect cell line Sf9 (derived from the fall armyworm *Spodoptera frugiperda*), for the expression of adf-3 and adf-4 using baculoviruses as vectors. Recombinant baculoviruses were generated containing partial cDNAs of adf-3 and adf-4 (14). In order to monitor synthesis, both proteins were provided with a His$_6$-Tag. To exclude artificial influences caused by the tag, versions without His$_6$-Tag were also employed.

The recombinant viruses were used to infect Sf9 cells for production of the spider silk proteins in the cytoplasm. After 3 days of incubation, infected cells were lyzed by sonification and insoluble cell contents were separated from soluble material by sedimentation. The sediment was dissolved in guanidinium thiocyanate (GdmSCN) prior to analysis by immunoblotting.

While a large fraction of ADF-3 was found to be soluble, ADF-4 was almost entirely insoluble three days after infection under the conditions employed (FIG. 1A) and independent from the presence of the His$_6$-Tag (FIG. 4A). Surprisingly, investigating the aggregates in adf-4 (SEQ NO: 2) expressing cells revealed filaments that coiled throughout the cytoplasm, whereby most of the cells contained only one or few filaments of a uniform width (FIG. 1B). In contrast, cells infected with control viruses or the adf-3 (SEQ NO: 1) encoding virus never produced such filaments (FIG. 4C, D). Immunofluorescence performed on the infected cells using anti-His$_6$ antibodies showed specific staining of the filaments thus confirming that the filaments were composed of ADF-4 (FIG. 1B).

Next, the inventors investigated whether ADF-3 and ADF-4 can co-assemble into filaments. The inventors generated a recombinant baculovirus containing both adf-3 (SEQ NO: 1) and adf-4 (SEQ NO: 2) under different and independent promoters, using the pFastbacDUAL donor plasmid. Infection of Sf9 cells with this virus resulted in synthesis of both proteins and the formation of protein filaments that showed similar appearance in comparison to the filaments formed by synthesis of ADF-4 alone (FIG. 4B). Interestingly, filaments assembled in the DUAL expression system were entirely formed by ADF-4 with no incorporated or stably associated ADF-3 (FIG. 1C and data not shown).

In order to study whether the apparent self-assembly is solely based on properties of ADF-4 or whether additional factors or modifications are involved, the inventors created a recombinant baculovirus coding for a secreted form of His$_6$-ADF-4. Infection of cells with this virus led to accumulation of ADF-4 in the culture media of the cells (FIG. 1D). Immunofluorescence revealed the abundance of ADF-4 containing secretory vesicles at the cell surface of the infected cells (FIG. 1E). Strikingly, the inventors did not observe any formation of ADF-4 filaments neither in compartments of the host cells nor in the culture media.

Silk thread formation generally depends on the protein concentration as well as on additional factors. Interestingly the intracellular pH 6.3 of Sf9 cells corresponds to the pH in the spinning dope prior to silk thread assembly (19). Further factors required for ADF-4 filament assembly in the cytosolic environment remain elusive. Investigating the self-assembling properties of ADF-4 in vitro stressed the importance of additional factors. Soluble ADF-4 was readily obtained by dissolving filaments in 6 M GdmSCN. Dissolved ADF-4 rapidly aggregated upon removal of GdmSCN by dialysis or dilution. However, the ADF-4 aggregates formed in vitro showed neither fibrillar structures nor did they display the chemical stability of ADF-4 filaments formed inside the Sf9 cells (see below and FIG. 4E, F). The above findings indicate the importance of the specific cytosolic environment, which may include additional, so far unresolved, cytoplasmatic factors important for controlled self-assembly.

Next the inventors characterized the morphology of ADF-4 filaments. The diameters of filaments ranged from 200 nm to 1 µm, however for each single filament the diameter was found to be constant. Furthermore, the filaments showed lengths up to 100 µm and often terminated in knots, branches or formed closed circles (FIG. 2A, D, E). Filaments displayed a smooth surface and were often associated with nanofibers (diameter ~5 nm) and other protein aggregates (FIG. 2). Immunoblotting, and immunoelectron microscopy indicated that filaments and associated assembly forms were composed of ADF-4 (FIG. 2C, 3A). Besides ADF-4 no other abundant protein could be detected in filaments as visualized by SDS-PAGE analysis followed by silver staining (FIG. 3A). The low number of filaments per cell and the recruitment of almost the entire cellular ADF-4 into the aggregates indicated that self-assembly of ADF-4 in Sf9 cells is likely to be a nucleated process, which previously has been also suggested for the silk spinning process of Bombyx mori (20).

Figure 3:
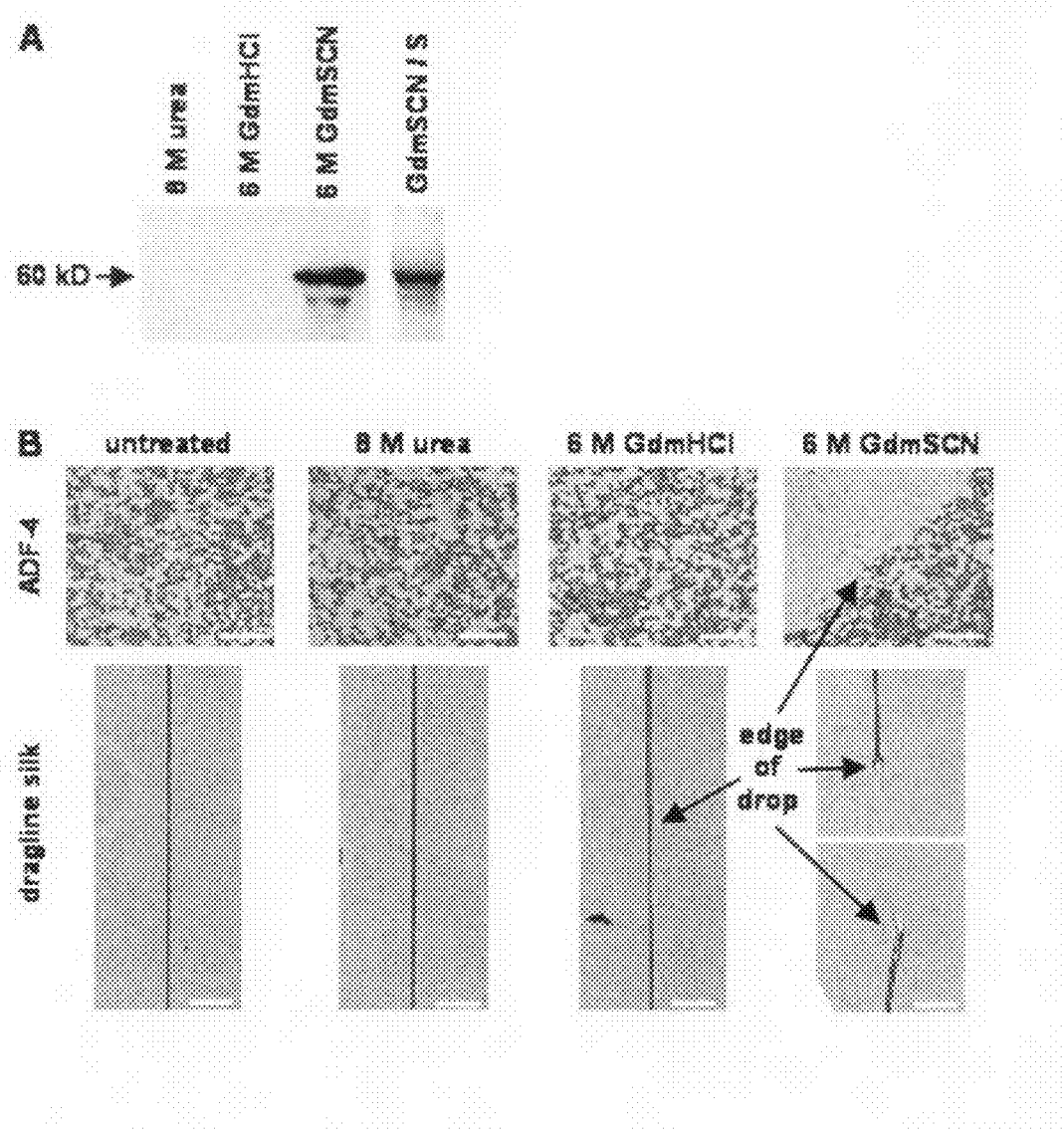
FIG. 3 Chemical stability of ADF-4 filaments and of dragline silk threads. (A) ADF-4 filaments were denatured as indicated. Undissolved filaments and aggregates did not enter the gel. Dissolved ADF-4 was detected by immunoblotting using an anti-His$_6$ antibody. Samples treated with 6M Gdm-SCN were also silver stained (GdmSCN/S). (B) Air dried ADF-4 filaments on mica and dragline silk threads on polypropylene were incubated for 30 seconds with ~0.1 µl of each solution as indicated. After rinsing with water samples were examined by light microscopy. Scale bar 25 µm.

The size of the filaments formed in the Sf9 cells seemed to be constrained by the volume of the cells making them too short for mechanical force measurements typically performed with silk threads (21). However, the inventors were able to analyze the chemical stability of wet and dry ADF-4 filaments in comparison to natural dragline silk threads of A. diadematus. Dragline threads have been reported to be insoluble in many denaturing agents (22). Application of 2% sodium dodecylsulfate (SDS) and 8 M urea apparently had no effect on the structure of ADF-4 filaments and dragline threads after 30 s of exposure (FIG. 3 and data not shown). Immersion of the filaments in 6 M guanidinium chloride (GdmCl) did not lead to solubilization of either ADF-4 filaments or dragline threads, although it did lead to swelling of dragline silk. Such swelling is likely caused by fibre supercontraction (21) which has previously been described for spider silks immersed in aqueous solutions and which results from reformation of hydrogen bonds in the amorphous matrix (21). In contrast to the denaturants mentioned above, a small drop of 6 M GdmSCN completely dissolved ADF-4 filaments as well as dragline threads within seconds (FIG. 3). In consequence the inventors conclude that both structures share molecular interactions, which are responsible for chemical resistance to specific denaturants.

Methods

Plasmid Construction.

The cDNAs of SEQ NO: 1 and 2 were cloned into pFastBac™ donor plasmids from Invitrogen. Sequences coding for peptide tags were provided 5'-terminal to the gene fragments. For His$_6$-tagged proteins, genes were excised from the host vector using SpeI/XhoI and ligated with equally digested pFastBac™HTa. For T7-taged (23) proteins, genes were first cloned into pET21 from Novagen using XhoI and EcoRI. The insert including the T7-Tag coding region was then excised with BglII and XhoI and ligated with pFastBac™1 digested with BamHI/XhoI. For co-expressing adf-3 (SEQ NO: 1) and adf-4 (SEQ NO: 2), both genes were cloned into pFasBac™DUAL and provided with sequences coding for T7- and S-Tags (24). The adf-4 (SEQ NO: 2) gene was excised from pET21-adf-4 (SEQ NO: 2) with BglII/XhoI and ligated with pFasBac™DUAL cleaved with NheI/BamHI. Two synthetic oligonucleotides (MWG Biotech) were annealed to provide an S-Tag coding sequence, which resulted in double stranded DNA with NheI/BamHI-compatible single strand extensions:

(SEQ ID NO: 5)
5'-CTAGCCCGGGATGAAAGAAACCGCTGCTGCTAAATTCGAACGCCAGC ACATGGACAGCGGTCGG-3'

(SEQ ID NO: 6)
5'-GATCCCGACCGCTGTCCATGTGCTGGCGTTCGAATTTAGCAGCAGCG GTTTCTTTCATCCCGGG-3' pET21-adf-3 (SEQ NO: 1) was digested with NheI/BamHI to remove the T7-Tag coding region. The vector was then ligated with the S-tag encoding DNA. The S-tagged adf-3 (SEQ NO: 1) was cloned into pFasBaC™DUAL-adf-4 (SEQ NO: 2) using XhoI/XmaI. In the dual construct, adf-3 and adf-4 were under the control of the independent p10 (25) and Polyhedrin (26) promoters. The sequence coding for the secretion signal of Honeybee melittin was amplified by PCR using the pMIBN5-HisA vector (Invitrogen) as template and the following primers containing CpoI restriction sites:

(SEQ ID NO: 7)
5'-CCTTCC<u>CGGTCCG</u>CCATGAAATTCTTAGTCAAC (SEQ ID NO: 8)
5'-CCTTCC<u>CGGACCGGG</u>CATAGATGTAAGAAAT

The resulting PCR product was cut with CpoI and ligated into pFastBaC™HTa-adf-4 (SEQ NO: 2) digested likewise. Positive clones were checked for orientation and correctness by sequencing.

Cell Culture

Sf9 (*Spodoptera frugiperda*; ATCC#: CRL-1711) cells were propagated at 27° C. in BIOINSECT-1 serum-free insect cell culture medium (Biological Industries). Sf9 cells were grown either as monolayers on cover slips in 6 well plates or in shaker flasks agitated at 80 rpm.

Production of Recombinant adf-3 (SEQ NO: 1) and adf-4 (SEQ NO: 2) Containing Baculovirus Competent *E. coli* DH10BAC cells, containing bacmid (baculovirus shuttle vector plasmid) and a helper plasmid, were used to generate recombinant bacmids according to the manufacturer's protocol (Invitrogen). Insertion of the gene into the bacmid was verified by PCR. Sf9 cells were transfected with recombinant bacmid DNA using ESCORT transfection reagent (Sigma-Aldrich) in 6-well plates. The cells were incubated for 5 h at 27° C., rinsed, and incubated for another 72 h. Media were harvested, centrifuged, and the virus-containing supernatant was tittered by plaque assays.

Expression of adf-3 and adf-4

Sf9 cells ($3 \times 10^6$ cells/ml) were infected with the recombinant viruses at various MOIs (multiplicity of infection) ranging from 0.1 to 10. Three days post infection (PI), cells were harvested by centrifugation at 500×g for 5 min.

Detection and Solubility of ADF-3 and ADF-4

Cells were resuspended at $1.2 \times 10^7$ cells/ml in 100 mM NaCl, 20 mM N-(2-hydroxyethyl)piperazine-N'-(2-ethanesulfonic acid) (HEPES), pH 7.5 and lyzed by sonification. Soluble and insoluble components were separated by centrifugation at 125,000×g for 30 min. For further analysis, pellets were resuspended in 6 M GdmSCN and dialyzed against 8 M Urea. Supernatant and pellet derived from $1.5 \times 10^5$ cells were loaded on 10% Tris-Glycine polyacrylamide gels under reducing conditions and blotted onto PVDF membranes (Millipore). Spider silk proteins were detected using a mouse anti-His$_6$ monoclonal antibody (Sigma-Aldrich, 1:10,000) or a mouse anti-T7 monoclonal antibody (Novagen, 1:10,000) and anti-mouse IgG peroxidase conjugate (Sigma-Aldrich, 1:5,000) as secondary antibody. An S-Protein peroxidase conjugate (Novagen, 1:5,000) was used to directly detect S-tagged ADF-3.

Immunocytochemistry

Cells grown on cover slips at 50% confluency were infected with adf-3 (SEQ NO: 1) or adf-4 (SEQ NO: 2) containing recombinant viruses at MOI=10. Three days PI cells were fixed with methanol at −20° C. Cover slips were incubated with mouse anti-His$_6$ monoclonal antibody (Roche) at a 1:300 dilution followed by Texas Red conjugated anti-mouse secondary IgG at 1:500 dilution. Cells were observed with an Olympus BX51 fluorescence microscope and images were taken with a Magnafire SP camera or analyzed by confocal microscopy.

ADF-4-Thread Purification

Cells were resuspended at $1.2 \times 10^7$ cells/ml in 100 mM NaCl, 20 mM HEPES, pH 7.5 and lyzed by adding 2% w/v sodium dodecylsulfate followed by incubation at 95° C. for 5 min. Threads were sedimented at 5,000×g followed by washing with 8 M urea and water$_{bidest}$.

Atomic Force (AFM), Scanning Electron (SEM) and Transmission Electron Microscopy (TEM)

Purified filaments were resuspended in water$_{bidest}$ and incubated for 3 min on freshly cleaved mica (AFM) or loaded on Thermanox® plastic cover slips (Nalgene Nunc) (SEM). For AFM, samples were rinsed with water$_{bidest}$ four times and air-dried prior to contact mode imaging using a Multimode SPM (Veeco). For SEM, samples were air dried after removal of the solution, vacuum coated with a gold layer and analyzed with a JSM-5900LV (JEOL Ltd.) at 20 kV. For TEM (JEOL Ltd.) analysis, filaments were adsorbed onto formvar coated grids and negatively stained with uranyl acetate. For immunostaining, fibers were incubated with mouse anti-His$_6$ antibodies followed by labeling with 18 nm gold-conjugated goat anti mouse IgG.

Thread Formation of ADF-4 Without His$_6$-Tag

To rule out possible influences of the His$_6$-tag on filament formation, T7-tagged ADF-4 was synthesized in Sf9 cells. The filament formation of T7-tagged ADF-4 was apparently indistinguishable to that of His$_6$-tagged ADF-4 (FIG. 4A).

Thread Formation in adf-3 (SEQ NO: 1) and adf-4 (SEQ NO: 2) Co-Expressing Cells

In Sf9 cells co-expressing adf-3 and adf-4, filaments could be detected that displayed an apparently indistinguishable morphology in comparison to filaments formed in cells producing only ADF-4 (FIG. 4B).

Expression of adf-3 (SEQ NO: 1) in Sf9 Cells

Although immunocytochemistry revealed fluorescent foci in adf-3 (SEQ NO: 1) expressing cells, filament-like structures could not be observed (FIG. 4C,D). Importantly, ADF-3 synthesized in Sf9 cells was largely soluble. Therefore foci formation represented sub-cellular accumulation rather than protein aggregation.

In Vitro Assembly of ADF-4

ADF-4 aggregated upon removal of denaturants by dialysis or after dilution into aqueous buffers. The resulting aggregates did not display any fibrillar morphology (FIG. 4E). Testing chemical stability revealed that in contrast to ADF-4 filaments, formed in the cytosol, the aggregates formed in vitro were soluble in 2% SDS or 8 M Urea (FIG. 4F).

Assembly of Spider Silk Derived Proteins

The following experiments were performed to demonstrate that proteins derived from spider silk sequences ADF-3 (SEQ ID NO:1) or ADF-4 (SEQ ID NO:2) can be assembled into morphological distinct forms. Proteins based on ADF-3 and ADF-4 were constructed, produced and prepared in aqueous solutions as described in Biochemistry 2004 Vol. 43 pp. 13604-11362 (27). If not otherwise mentioned protein solutions contained 10 mM Tris-(hydroxymethyl)-aminomethan (Tris) pH 8.0.

1. Spheres

Protein spheres displaying diameters ranging between 0.5 and 2 μm (FIG. 5*a*) were generated by adding 0.8 M ammonium sulphate to a 0.2% (w/v) ADF-4 based protein solution.

2. Nanofibrils

Nanofibrils displaying diameters between 0.7 and 4 nm (FIG. 5*b*) were formed by incubating a 1% (w/v) ADF-4 based protein solution at room temperature for 2 weeks.

3. Microfibrils

Figure 5:
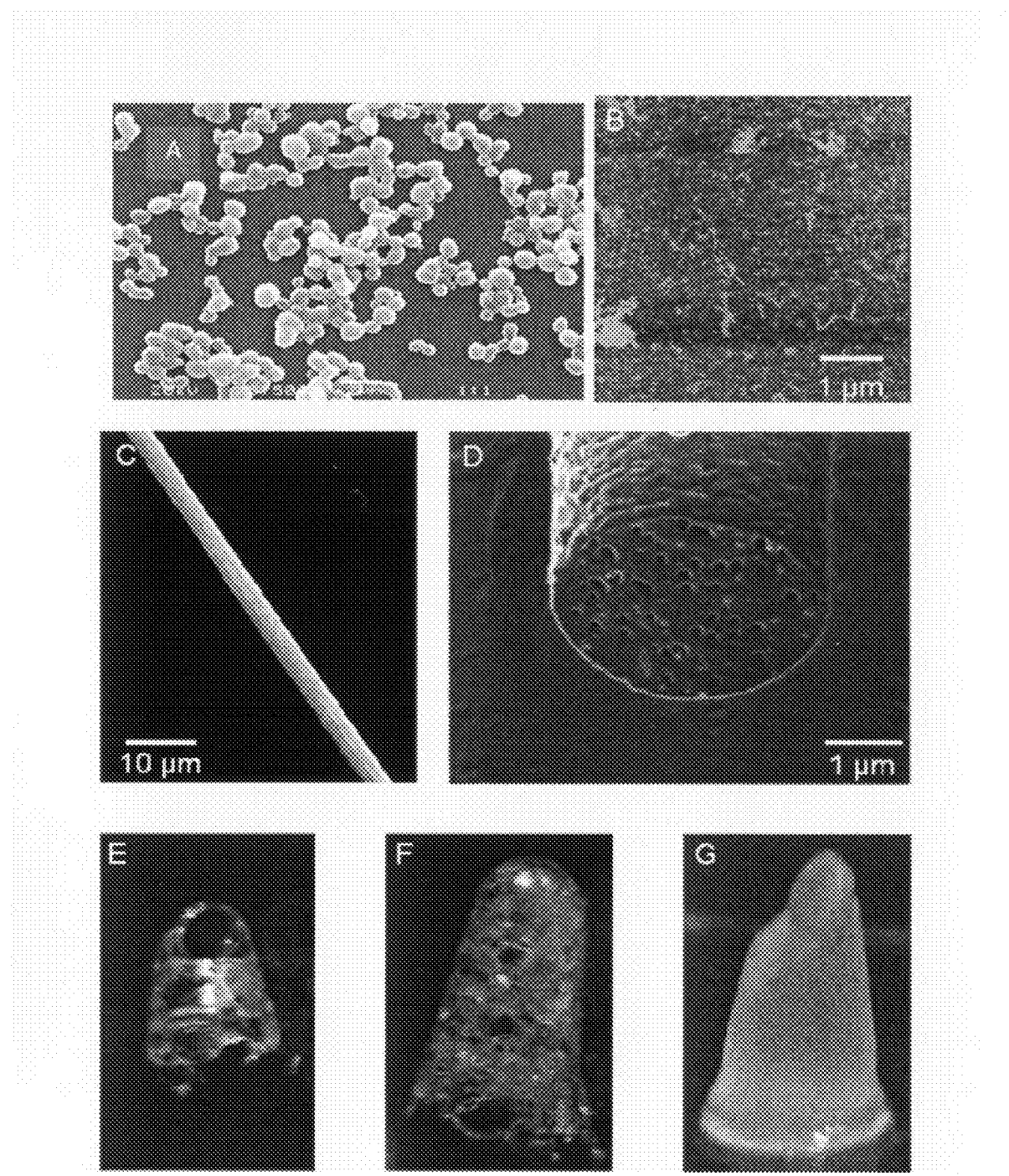
FIG. 5: Assembly forms of spider silk proteins. (A) Spheres formed by proteins based on ADF-4 visualized by scanning electron microscopy (SEM). (B) Nanofibrils formed by proteins based on ADF-4 visualized by atomic force microscopy (height information). (C, D) Microfibril formed by proteins based on ADF-3 investigated by SEM (C). For cutting the fibril and subsequent visualization of the cross section a focused Ga$^+$ ion beam was used (D). (E) Foam generated from a protein solution based on ADF-3. (F) Foam generated from a solution based on ADF-4. (G) Crosslinked gel formed by ADF-4 nanofibrils. ADF-3 and ADF-4 as described in FIG. 5 correspond to SEQ ID NO: 1 and 2, respectively.

For the formation of microfibrils 5-10 μl of a 25% (w/v) ADF-3 based protein solution was slowly injected into 0.5 M potassium phosphate pH 8.0, forming a stable drop of protein solution. After incubation for 1 min the protein drop was removed from the solution using tweezers. After an additional incubation time of 1 min in air a protein fibril could be drawn from the protein drop at a rate of approximately 2 cm/s using a second set of tweezers. The fibrils displayed a round cross section with a diameter of 4 μm (FIG. 5*c,d*).

4. Foams

Protein foams (FIG. 5*e,f*) were generated from solutions containing 2.5 mM ammonium peroxodisulfate (APS), 100 μM tris(2,2'-bipyridyl)dichlororuthenium(II) (Rubpy) and 10% (w/v) ADF-3 based protein or 2% (w/v) ADF-4 based protein. The protein solutions were frothed up with air. To stabilize the resulting foam structure proteins were crosslinked by exposition to visible light from a tungsten lamp for 1 min (28). Foams were subsequently dried at 95° C.

5. Gels

ADF-4 based nanofibrils at 1% (w/v) concentration (see section 2) displayed a gel like appearance which easily could be disrupted by agitation or shearing. To improve the mechanical properties of the gel APS and Rubpy were allowed to enter the gel by diffusion to yield final concentrations of 10 mM APS and 100 µM Rubpy. After light induced crosslinking (see section 4) dimensionally stable gels could be obtained (FIG. 5g).

6. Films

Figure 6:
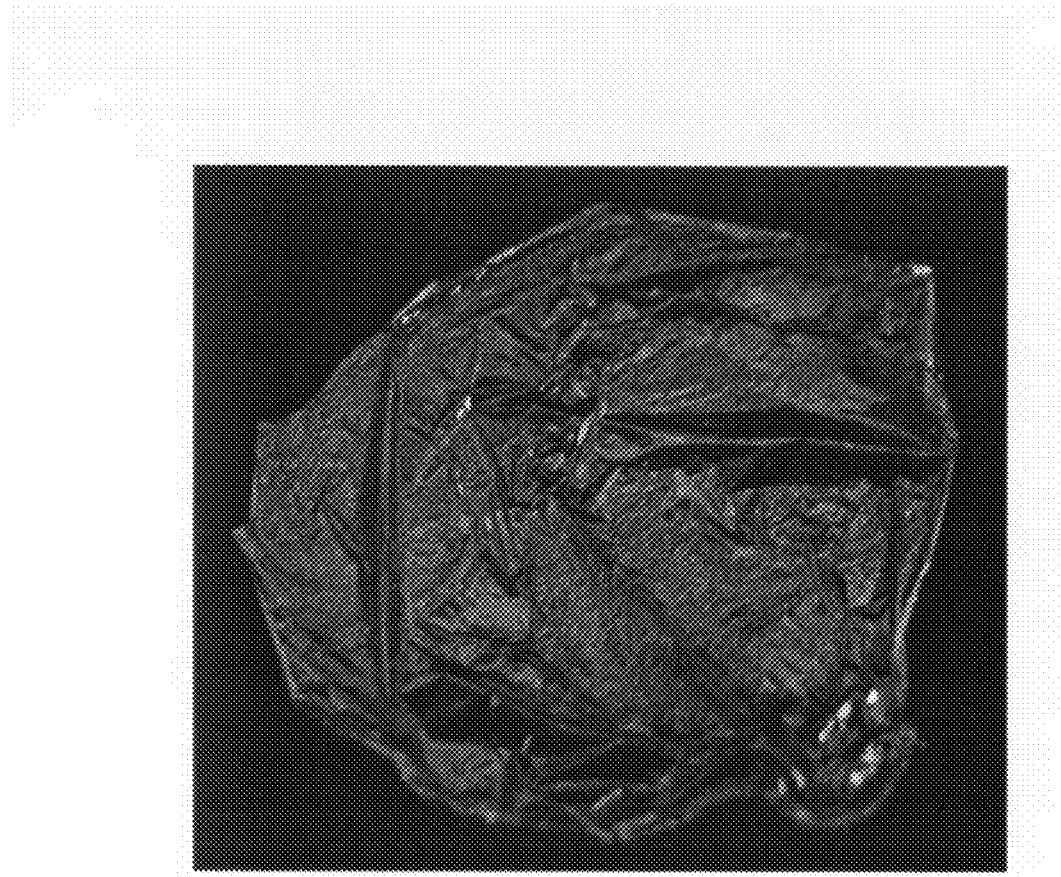
FIG. 6: A film produced from spider silk proteins of the invention. ADF-3 derived protein was dissolved in 1,1,1,3,3,3-Hexafluor-2-propanol at 20 mg/ml concentration. 200 µl of the solution were spread on a polystyrene surface (ca. 20 cm$^2$). After evaporation of the solvent a transparent protein film could be pulled off.

ADF-3 derived protein was dissolved in 1,1,1,3,3,3-Hexafluor-2-propanol at 20 mg/ml concentration. 200 µl of the solution were spread on a polystyrene surface (ca. 20 cm$^2$). After evaporation of the solvent a transparent protein film could be pulled off (see FIG. 6).

REFERENCES

1. J. M. Gosline, P. A. Guerette, C. S. Ortlepp, K. N. Savage, *J. Exp. Biol.* 202 Pt 23, 3295-3303 (1999).
2. J. Warwicker, *J. Mol. Biol.* 2, 350-362 (1960).
3. A. H. Simmons, E. Ray, L. W. Jelinski, *Macromolecules* 27, 5235-5237 (1994).
4. A. D. Parkhe, S. K. Seeley, K. Gardner, L. Thompson, R. V. Lewis, *J. Mol. Recognit.* 10, 1-6 (1997).
5. J. D. van Beek, S. Hess, F. Vollrath, B. H. Meier, *Proc. Natl. Acad. Sci. U.S.A* 99, 10266-10271 (2002).
6. D. H. Hijirida et al., *Biophys. J.* 71, 3442-3447 (1996).
7. K. Kerkam, C. Viney, D. Kaplan, S. Lombardi, *Nature* 349, 596-598 (1991).
8. D. P. Knight and F. Vollrath, *Proc. R. Soc. Lond.* 519-523 (1999).
9. D. P. Knight and F. Vollrath, *Naturwissenschaften* 88, 179-182 (2001).
10. F. Vollrath, D. Knight, X. W. Hu, *Proc. R. Soc. Lond B Biol. Sci.* 265, 817-820 (1998).
11. E. K. Tillinghast, S. F. Chase, M. A. Townley, *J. Insect Physiol.* 30, 591-596 (1984).
12. D. P. Knight, M. M. Knight, F. Vollrath, *Int. J. Biol. Macromol.* 27, 205-210 (2000).
13. S. Winkler and D. L. Kaplan, *J. Biotechnol.* 74, 85-93 (2000).
14. P. A. Guerette, D. G. Ginzinger, B. H. Weber, J. M. Gosline, *Science* 272, 112-115 (1996).
15. J. Gatesy, C. Hayashi, D. Motriuk, J. Woods, R. Lewis, *Science* 291, 2603-2605 (2001).
16. S. Arcidiacono, C. Mello, D. Kaplan, S. Cheley, H. Bayley, *Appl. Microbiol. Biotechnol.* 49, 31-38 (1998).
17. J. Scheller, K. H. Guhrs, F. Grosse, U. Conrad, *Nat. Biotechnol.* 19, 573-577 (2001).
18. A. Lazaris et al., *Science* 295, 472-476 (2002).
19. V. Vachon, M. J. Paradis, M. Marsolais, J. L. Schwartz, R. Laprade, *Biochemistry* 34, 15157-15164 (1995).
20. G. Li et al., *Eur. J. Biochem.* 268, 6600-6606 (2001).
21. Z. Shao, R. J. Young, F. Vollrath, *Int. J. Biol. Macromol.* 24, 295-300 (1999).
22. S. Lombardi and D. Kaplan, *J. Arachnol.* 18, 297-306 (1990).
23. Kroll, D. J. et al. *DNA Cell Biol.* 12, 441-453 (1993).
24. Kim, J. S. & Raines, R. T. *Protein Sci.* 2, 348-356 (1993).
25. Knebel, D., Lubbert, H. & Doerfler, W. *EMBO J.* 4, 1301-1306 (1985).
26. Smith, G. E., Summers, M. D. & Fraser, M. *J. Mol. Cell. Biol.* 3, 2156-2165 (1983).
27. Huemmerich, D., Helsen, C. W., Oschmann, J., Rudolph, R. & Scheibel, T. *Biochemistry* 43, 13604-13612 (2004)
28. Fancy, D. A. & Kodadek, T. *Proc. Natl. Acad. Sci. U.S.A* 96, 6020-6024 (1999)

What is claimed is:

1. A synthesized spider dragline protein, which comprises the amino acid sequence encoded by the nucleic acid sequence of SEQ ID NO: 2 or a variant thereof, wherein the variant is defined as having one amino acid substitution, one to five amino acid insertions, and/or one to five amino acid deletions as compared to the amino acid sequence encoded by the nucleic acid sequence of SEQ ID NO:2, and wherein said variant retains tensile strength, elasticity, and ability to form a thread of the amino acid sequence encoded by the nucleic acid sequence of SEQ ID NO: 2.

2. A gel or a foam comprising or consisting of a protein of claim 1.

3. Coatings for implants and stents comprising or consisting of a protein of claim 1.

4. A thread or fiber, comprising a protein of claim 1 and a further fiber, the further fiber being not of spider origin.

5. A film comprising or consisting of a protein of claim 1.

6. Wound closure or coverage systems, suture materials, replacement materials, which are obtainable using a protein of claim 1.

7. A thread, which comprises a spider dragline protein of claim 1.

8. The thread or fiber according to claim 4, wherein the further fiber being not of spider origin is a plant derived fiber or synthetic fiber.

9. The replacement materials according to claim 6, further comprising artificial cartilage or tendon materials.

10. The protein of claim 1, wherein said protein comprises the amino acid sequence encoded by the nucleic acid sequence of SEQ ID NO:2.

11. Wound closure or coverage systems, suture materials, replacement materials, which are obtainable using a thread of claim 7.

* * * * *

SEQUENCE LISTING

<160> NUMBER OF SEQ ID NOS: 8

<210> SEQ ID NO 1
<211> LENGTH: 1914
<212> TYPE: DNA
<213> ORGANISM: Araneus diadematus

<400> SEQUENCE: 1

```
gcacgagccg gatctggaca acaaggaccc ggacaacaag gacccggaca acaaggaccc      60
ggacaacaag gaccatatgg acccggtgca tccgccgcag cagcagccgc tggaggttat     120
ggacccggat ctggacaaca aggacccagc caacaaggac ctggccaaca aggacccggt     180
ggtcaaggac catatggacc cggtgcatcc gccgccgcag cagccgctgg tggatatgga     240
cccggttccg gacaacaagg accaggaggt caaggaccat atggacctgg ttcatccgct     300
gccgcagcag ccgctggagg taatggaccc ggatctggac aacaagggcc cggtcaacaa     360
ggtcctggac aacaaggacc cggtgcatcc gccgccgcag cagccgctgg aggatacgga     420
cccggatctg gacaacaagg acccgacaa caaggaccag gaggtcaagg accatatgga     480
cctggtgcat ccgccgctgc agcagccgct ggaggatacg gacccggatc tggacaacaa     540
ggacccggac aacaaggacc aggaggtcaa ggaccatatg gacccggtgc atccgctgca     600
gcagcagccg ctggaggtta tggacccgga tctggacaac aaggacccgg acaacaagga     660
cctggacaac aaggacccgg tggtcaagga ccatatggac ccggtgcatc cgccgccgca     720
gcagccgctg gaggatacgg acccggttat ggacagcaag gaccaggaca acaaggacca     780
```

-continued

| | |
|---|---|
| ggaggtcaag gaccatatgg acctggtgca tccgccgcct cagcagcctc tggaggatac | 840 |
| ggaccccggat ctggacaaca aggacccgga caacaaggac ctggaggtca aggaccatat | 900 |
| ggacctggtg catccgccgc agcagcagcc gctggaggtt atggacccgg atctggacaa | 960 |
| caaggaccag gccaacaagg acccggtcaa caaggacctg acaacaagg acccggtggt | 1020 |
| caaggaccat atggacctgg tgcatccgcc gcagcagcag ccgctggagg ttatggaccc | 1080 |
| ggatctggac aacaaggacc cggtcaacaa ggacccggtc aacaaggacc cggtcaacaa | 1140 |
| ggacccggtc aacaaggacc cggccaacaa ggacccggtc aacaaggacc cggccaacaa | 1200 |
| ggacctggtc aacaaggtcc cggtggtcaa ggggcatatg gacctggtgc atccgccgca | 1260 |
| gcaggagccg ctggaggtta tggacccgga tctggacaac aaggacccgg acaacaagga | 1320 |
| cccggacaac aaggacccgg acaacaagga cccggacaac aaggacccgg acaacaagga | 1380 |
| cccggacaac aaggacccgg acaacaagga ccatatggac ctggtgcatc cgccgcagca | 1440 |
| gcagccgctg gaggttatgg acccggatct ggacaacaag acccggcca acaaggacct | 1500 |
| ggacaacaag gacccgttgg tcaaggacca tatggacctg gtgcggcttc tgcagctgta | 1560 |
| tctgttggag atatggacc acaaagctcc tcggctcctg ttgcatcagc agccgcttct | 1620 |
| cgccttcttt ctccagcggc cagttctaga gtttcatcgg ctgtatcatc tttggtatct | 1680 |
| agtggaccta ctaatcaagc tgcactttct aatactatca gtagcgttgt atcgcaagtt | 1740 |
| agtgcaagta atcctggtct ttctggttgc gatgtacttg tgcaagcatt gctcgaagtt | 1800 |
| gtatcggccc tggtatctat ccttggatct tctagtatcg gcaaattaa ctatggtgcc | 1860 |
| tctgctcagt acacccaaat ggtaggtcaa tctgtagctc aagcccttgc ttaa | 1914 |

<210> SEQ ID NO 2
<211> LENGTH: 1971
<212> TYPE: DNA
<213> ORGANISM: Araneus diadematus

<400> SEQUENCE: 2

| | |
|---|---|
| gcaggatctt cagcagcagc ggccgcggca gcaagtggat ctggaggata cggacctgaa | 60 |
| aaccaaggac catctggacc tgtagcatat ggacctggtg acccgtatc ttcagctgca | 120 |
| gcagcagccg ctgcaggaag tggacctggt ggatacggac ctgaaaacca aggaccatct | 180 |
| ggaccccgag gatatggacc tggtggttcc ggatcttcag cagcagcagc agccgctgca | 240 |
| gcaagtggac ctggaggata tggacctgga agccaaggac catctggacc tggtggatcc | 300 |
| ggaggatatg gtcccggaag ccaagggcca tctggacctg gtgcatcttc ggcagcagca | 360 |
| gcagccgctg cagcaagtgg acctggagga tatggacctg gaagccaagg accatctgga | 420 |
| cctggagcat atggacctgg tgacccggga tcttcagctg cagcaagtgg acctggagga | 480 |
| tatggacctg gaagccaagg accatctgga cctggtggat ccggaggata tggtcccgga | 540 |
| agccaagggc catctggacc tggtgggcct ggtgcatctg cggcagcagc agcagccgct | 600 |
| gcagcaagtg gacctggagg atatggacct ggaagccaag gaccatctgg acctggagca | 660 |
| tatggacctg gtggacccgg atcttcagct gcagcaagtg gacctggagg atatggacct | 720 |
| ggaagccaag gaccatctgg acctggagca tatggacctg gtggacccgg atcttcagct | 780 |
| gcagcagcag ccgctgcagg aagtggacct ggtggatacg gacctggaaa ccaaggacca | 840 |
| tctggacccg aggatatgg acctggtggt cccggatctt cagcagcagc agccgctgca | 900 |
| gcaagtggac ctggaggata tggacctgga agccaaggac catctggacc tggagtatat | 960 |
| ggacctggtg gacccggatc ttcagctgca gcagcagccg ctgcaggaag tggacctggt | 1020 |

-continued

```
ggatacggac ctggaaacca aggaccatct ggacccggag gatatggacc tggtggttcc    1080
ggatcttcag cagcagcagc agccgctgca gcaagtggac ctggaggata tggacctgga    1140
agccaaggac catctggacc tggtggatcc ggaggatatg gtcccggaag ccaagggcca    1200
tctggacctg gtgcatcttc ggcagcagca gcagccgctg cagcaagtgg acctggagga    1260
tatggacctg gaagccaagg accatctgga cctggagcat atggacctgg tgacccgga    1320
tcttcagctg cagcaagtgg acctggagga tatggacctg gaagccaagg accatctggt    1380
cctggagcat atggacctgg tgacccggga tcttcagctg cagcagccgc tgcagcaagt    1440
ggacctggag gatatggacc tggaagccaa ggaccatctg gacctggtgg atcccgagga    1500
tatggtcccg gaagccaagg acctggtggg cctggagcat ctgcggcagc agcagcagcc    1560
gctgcagcaa gtggacctgg aggatatgga cctggaagcc aaggaccatc tggacctgga    1620
tatcaaggcc ctagtggtcc tggagcatat ggcccatctc cttctgcttc cgcatccgtt    1680
gcagcctctc gtttatcttc gcctgcagcc tcgtctagag tgtcttccgc tgtatcgtct    1740
ttagtgtcta gcggacctac gaatggtgct gctgtttctg gagctttgaa tagtttagta    1800
tctcagatta gtgcaagtaa tccaggttta tcgggatgtg atgctcttgt gcaggcatta    1860
ttggaattag tgtctgctct tgtggcaatt ctttcatctg caagtattgg ccaagtcaac    1920
gtcagctctg ttagtcagtc aactcaaatg attagccaag ctctttcata a             1971
```

<210> SEQ ID NO 3
<211> LENGTH: 636
<212> TYPE: PRT
<213> ORGANISM: Araneus diadematus

<400> SEQUENCE: 3

```
Ala Arg Ala Gly Ser Gly Gln Gln Gly Pro Gly Gln Gln Gly Pro Gly
1               5                   10                  15

Gln Gln Gly Pro Gly Gln Gln Gly Pro Tyr Gly Pro Gly Ala Ser Ala
            20                  25                  30

Ala Ala Ala Ala Ala Gly Gly Tyr Gly Pro Gly Ser Gly Gln Gln Gly
        35                  40                  45

Pro Ser Gln Gln Gly Pro Gly Gln Gln Gly Pro Gly Gly Gln Gly Pro
    50                  55                  60

Tyr Gly Pro Gly Ala Ser Ala Ala Ala Ala Ala Gly Gly Tyr Gly
65                  70                  75                  80

Pro Gly Ser Gly Gln Gln Gly Pro Gly Gln Gln Gly Pro Tyr Gly Pro
                85                  90                  95

Gly Ser Ser Ala Ala Ala Ala Ala Gly Gly Asn Gly Pro Gly Ser
            100                 105                 110

Gly Gln Gln Gly Ala Gly Gln Gln Gly Pro Gly Gln Gln Gly Pro Gly
        115                 120                 125

Ala Ser Ala Ala Ala Ala Ala Gly Gly Tyr Gly Pro Gly Ser Gly
    130                 135                 140

Gln Gln Gly Pro Gly Gln Gln Gly Pro Gly Gly Gln Gly Pro Tyr Gly
145                 150                 155                 160

Pro Gly Ala Ser Ala Ala Ala Ala Ala Gly Gly Tyr Gly Pro Gly
                165                 170                 175

Ser Gly Gln Gly Pro Gly Gln Gln Gly Pro Gly Gln Gln Gly Pro Tyr
            180                 185                 190

Gly Pro Gly Ala Ser Ala Ala Ala Ala Ala Gly Gly Tyr Gly Pro
        195                 200                 205
```

-continued

Gly Ser Gly Gln Gln Gly Pro Gly Gln Gln Gly Pro Gly Gln Gln Gly
        210                 215                 220

Pro Gly Gly Gln Gly Pro Tyr Gly Pro Gly Ala Ser Ala Ala Ala Ala
225                 230                 235                 240

Ala Ala Gly Gly Tyr Gly Pro Gly Tyr Gly Gln Gln Gly Pro Gly Gln
            245                 250                 255

Gln Gly Pro Gly Gln Gly Pro Tyr Gly Pro Gly Ala Ser Ala Ala
        260                 265                 270

Ser Ala Ala Ser Gly Gly Tyr Gly Pro Gly Ser Gly Gln Gln Gly Pro
    275                 280                 285

Gly Gln Gln Gly Pro Gly Gln Gly Pro Tyr Gly Pro Gly Ala Ser
        290                 295                 300

Ala Ala Ala Ala Ala Ala Gly Gly Tyr Gly Pro Gly Ser Gly Gln Gln
305                 310                 315                 320

Gly Pro Gly Gln Gln Gly Pro Gly Gln Gln Gly Pro Gly Gln Gln Gly
            325                 330                 335

Pro Gly Gly Gln Gly Pro Tyr Gly Pro Gly Ala Ser Ala Ala Ala Ala
        340                 345                 350

Ala Ala Gly Gly Tyr Gly Pro Gly Ser Gly Gln Gln Gly Pro Gly Gln
            355                 360                 365

Gln Gly Pro Gly Gln Gln Gly Pro Gly Gln Gln Gly Pro Gly Gln Gln
        370                 375                 380

Gly Pro Gly Gln Gln Gly Pro Gly Gln Gln Gly Pro Gly Gln Gln Gly
385                 390                 395                 400

Pro Gly Gln Gln Gly Pro Gly Gln Gly Ala Tyr Gly Pro Gly Ala
            405                 410                 415

Ser Ala Ala Ala Gly Ala Ala Gly Gly Tyr Gly Pro Gly Ser Gly Gln
            420                 425                 430

Gln Gly Pro Gly Gln Gln Gly Pro Gly Gln Gln Gly Pro Gly Gln Gln
        435                 440                 445

Gly Pro Gly Gln Gln Gly Pro Gly Gln Gln Gly Pro Gly Gln Gln Gly
    450                 455                 460

Pro Gly Gln Gln Gly Pro Tyr Gly Pro Gly Ala Ser Ala Ala Ala Ala
465                 470                 475                 480

Ala Ala Gly Gly Tyr Gly Pro Gly Ser Gly Gln Gln Gly Pro Gly Gln
            485                 490                 495

Gln Gly Pro Gly Gln Gln Gly Pro Gly Gln Gly Pro Tyr Gly Pro
        500                 505                 510

Gly Ala Ala Ser Ala Ala Val Ser Val Gly Gly Tyr Gly Pro Gln Ser
        515                 520                 525

Ser Ser Val Pro Val Ala Ser Ala Val Ala Ser Arg Leu Ser Ser Pro
530                 535                 540

Ala Ala Ser Ser Arg Val Ser Ser Ala Val Ser Ser Leu Val Ser Ser
545                 550                 555                 560

Gly Pro Thr Lys His Ala Ala Leu Ser Asn Thr Ile Ser Ser Val Val
            565                 570                 575

Ser Gln Val Ser Ala Ser Asn Pro Gly Leu Ser Gly Cys Asp Val Leu
        580                 585                 590

Val Gln Ala Leu Leu Glu Val Val Ser Ala Leu Val Ser Ile Leu Gly
    595                 600                 605

Ser Ser Ser Ile Gly Gln Ile Asn Tyr Gly Ala Ser Ala Gln Tyr Thr
    610                 615                 620

Gln Met Val Gly Gln Ser Val Ala Gln Ala Leu Ala
625                 630                 635

<210> SEQ ID NO 4
<211> LENGTH: 410
<212> TYPE: PRT
<213> ORGANISM: Araneus diadematus

<400> SEQUENCE: 4

Ala Gly Ser Ser Ala Ala Ala Ala Ala Ser Gly Ser Gly Gly
1               5                   10                  15

Tyr Gly Pro Glu Asn Gln Gly Pro Ser Gly Pro Val Ala Tyr Gly Pro
            20                  25                  30

Gly Gly Pro Val Ser Ser Ala Ala Ala Ala Ala Ala Gly Ser Gly
            35                  40                  45

Pro Gly Gly Tyr Gly Pro Glu Asn Gln Gly Pro Ser Gly Pro Gly Gly
50                  55                  60

Tyr Gly Pro Gly Gly Ser Gly Ser Ala Ala Ala Ala Ala Ala Ala
65                  70                  75                  80

Ala Ser Gly Pro Gly Gly Tyr Gly Pro Gly Ser Gln Gly Pro Ser Gly
            85                  90                  95

Pro Gly Gly Ser Gly Gly Tyr Gly Pro Gly Ser Gln Gly Ala Ser Gly
            100                 105                 110

Pro Gly Gly Pro Gly Ala Ser Ala Ala Ala Ala Ala Ala Ala Ala
            115                 120                 125

Ala Ser Gly Pro Gly Gly Tyr Gly Pro Gly Ser Gln Gly Pro Ser Gly
130                 135                 140

Pro Gly Ala Tyr Gly Pro Gly Gly Pro Gly Ser Ser Ala Ala Ala Ala
145                 150                 155                 160

Ala Ala Ala Ala Ser Gly Pro Gly Gly Tyr Gly Pro Gly Ser Gln Gly
            165                 170                 175

Pro Ser Gly Pro Gly Val Tyr Gly Pro Gly Gly Pro Gly Ser Ser Ala
            180                 185                 190

Ala Ala Ala Ala Ala Gly Ser Gly Pro Gly Gly Tyr Gly Pro Glu
            195                 200                 205

Asn Gln Gly Pro Ser Gly Pro Gly Tyr Gly Pro Gly Gly Ser Gly
210                 215                 220

Ser Ser Ala Ala Ala Ala Ala Ala Ala Ser Gly Pro Gly Gly Tyr
225                 230                 235                 240

Gly Pro Gly Ser Gln Gly Pro Ser Gly Pro Gly Gly Ser Gly Gly Tyr
            245                 250                 255

Gly Pro Gly Ser Gln Gly Gly Ser Gly Pro Gly Ala Ser Ala Ala Ala
            260                 265                 270

Ala Ala Ala Ala Ser Gly Pro Gly Gly Tyr Gly Pro Gly Ser Gln
            275                 280                 285

Gly Pro Ser Gly Pro Gly Tyr Gln Gly Pro Ser Gly Pro Gly Ala Tyr
            290                 295                 300

Gly Pro Ser Pro Ser Ala Ser Ala Ser Val Ala Ala Ser Val Tyr Leu
305                 310                 315                 320

Arg Leu Gln Pro Arg Leu Glu Val Ser Ser Ala Val Ser Ser Leu Val
            325                 330                 335

Ser Ser Gly Pro Thr Asn Gly Ala Ala Val Ser Gly Ala Leu Asn Ser
            340                 345                 350

Leu Val Ser Gln Ile Ser Ala Ser Asn Pro Gly Leu Ser Gly Cys Asp
            355                 360                 365

Ala Leu Val Gln Ala Leu Leu Glu Leu Val Ser Ala Leu Val Ala Ile
            370                 375                 380

```
Leu Ser Ser Ala Ser Ile Gly Gln Val Asn Val Ser Val Ser Gln
385                 390                 395                 400

Ser Thr Gln Met Ile Ser Gln Ala Leu Ser
                405                 410

<210> SEQ ID NO 5
<211> LENGTH: 64
<212> TYPE: DNA
<213> ORGANISM: Artificial Sequence
<220> FEATURE:
<223> OTHER INFORMATION: Artifically synthesized oligonucleotide primer

<400> SEQUENCE: 5
ctagcccggg atgaaagaaa ccgctgctgc taaattcgaa cgccagcaca tggacagcgg      60
tcgg                                                                  64

<210> SEQ ID NO 6
<211> LENGTH: 64
<212> TYPE: DNA
<213> ORGANISM: Artificial Sequence
<220> FEATURE:
<223> OTHER INFORMATION: Artifically synthesized oligonucleotide primer

<400> SEQUENCE: 6
gatcccgacc gctgtccatg tgctggcgtt cgaatttagc agcagcggtt tctttcatcc      60
cggg                                                                  64

<210> SEQ ID NO 7
<211> LENGTH: 33
<212> TYPE: DNA
<213> ORGANISM: Artificial Sequence
<220> FEATURE:
<223> OTHER INFORMATION: Artifically synthesized oligonucleotide primer

<400> SEQUENCE: 7
ccttcccggt ccgccatgaa attcttagtc aac                                  33

<210> SEQ ID NO 8
<211> LENGTH: 31
<212> TYPE: DNA
<213> ORGANISM: Artificial Sequence
<220> FEATURE:
<223> OTHER INFORMATION: Artifically synthesized oligonucleotide primer

<400> SEQUENCE: 8
ccttcccgga ccgggcatag atgtaagaaa t                                    31
```